(12) United States Patent
Wang et al.

(10) Patent No.: US 7,420,663 B2
(45) Date of Patent: Sep. 2, 2008

(54) SPECTROSCOPIC SENSOR ON MOBILE PHONE

(75) Inventors: Sean Xiaolu Wang, Wilmington, DE (US); Xin Jack Zhou, Hockessin, DE (US)

(73) Assignee: BWT Property Inc., Newark, DE (US)

( * ) Notice: Subject to any disclaimer, the term of this patent is extended or adjusted under 35 U.S.C. 154(b) by 88 days.

(21) Appl. No.: 11/419,823

(22) Filed: May 23, 2006

(65) Prior Publication Data

US 2006/0279732 A1 Dec. 14, 2006

Related U.S. Application Data

(60) Provisional application No. 60/594,976, filed on May 24, 2005.

(51) Int. Cl.
*G01J 3/28* (2006.01)
(52) U.S. Cl. .......................... 356/72; 356/326; 356/328; 356/419
(58) Field of Classification Search ................... 356/72, 356/301, 326, 328, 317, 318
See application file for complete search history.

(56) References Cited

U.S. PATENT DOCUMENTS 4,822,169 A * 4/1989 Distl et al. ................... 356/364
5,175,697 A * 12/1992 Kawagoe et al. ............. 356/320
5,428,558 A * 6/1995 Cahill et al. ................. 356/319
6,490,075 B1 * 12/2002 Scheps et al. ................ 359/285
6,580,935 B1 * 6/2003 Wach et al. .................. 600/310
6,947,571 B1 9/2005 Rhoads et al.
7,049,597 B2 * 5/2006 Bodkin ........................ 250/353
7,283,238 B2 * 10/2007 Simons et al. ............... 356/402
2003/0136837 A1 7/2003 Amon et al.
2003/0187742 A1 10/2003 Yamagishi
2003/0193589 A1 * 10/2003 Lareau et al. ................ 348/294
2005/0111723 A1 5/2005 Hannigan et al.
2006/0082760 A1 4/2006 Lin
2006/0111620 A1 * 5/2006 Squilla et al. ............... 600/300
2006/0206010 A1 * 9/2006 Iida et al. .................... 600/300
2006/0222567 A1 * 10/2006 Kloepfer et al. ............. 422/68.1

FOREIGN PATENT DOCUMENTS

WO WO 2004/098402 A1 * 11/2004

* cited by examiner

*Primary Examiner*—F. L Evans
(74) *Attorney, Agent, or Firm*—Frank F. Tian (57) ABSTRACT

This invention discloses a spectroscopic sensor that is integrated with a mobile communication device, such as a mobile phone. The spectroscopic sensor is capable of measuring the optical spectra of a physical object for purposes of detection, identification, authentication, and real time monitoring. Through the mobile communication device, the obtained spectral information can be transmitted, distributed, collected, and shared by utilizing all the functions of the known or existing wireless communication networks.

16 Claims, 8 Drawing Sheets

SPECTROSCOPIC SENSOR ON MOBILE PHONE

REFERENCE TO RELATED APPLICATIONS

This application claims an invention which was disclosed in Provisional Patent Application No. 60/594,976, filed May 24, 2005, entitled "Spectroscopic Sensor on Mobile Phone". The benefit under 35 USC § 119(e) of the above mentioned United States Provisional Applications is hereby claimed, and the aforementioned application is hereby incorporated herein by reference.

FIELD OF THE INVENTION

The present invention relates generally to optical spectroscopic sensors and more specifically to an optical spectroscopic sensor integrated with a mobile communication device to utilize various functions of a wireless communication network.

BACKGROUND

Mobile communication devices, especially mobile phones, have become a convenient means for information exchange. Recently, their function has been extended from a mere communicational tool to an information collection tool as well. One example is the mobile phone with a built-in digital camera. The pictures taken by the camera can be transmitted in real time via a wireless communication system and shared among a group of people.

More functions can be built into a mobile communication device by utilizing its information transmission capability.

In U.S. Pat. No. 6,947,571 to Rhoads et al (hereinafter merely Rhoads), describes a cell phone equipped with a 2D optical sensor, which enables a variety of applications. For example, such a phone may also be provided with a digital watermark decoder, permitting decoding of steganographic data on imaged objects. Movement of a phone may be inferred by sensing movement of an imaged pattern across the optical sensor's field of view, allowing use of the phone as a gestural input device through which a user can signal instructions to a computer-based process. A variety of other arrangements by which electronic devices can interact with the physical world are also detailed, e.g., involving sensing and responding to digital watermarks, bar codes, RFIDs, etc.

In U.S. Patent Application No. 2003/0187742 to Junichi Yamagishi, (hereinafter merely Yamagishi), describes a program for personal authentication using a mobile phone that enables the mobile phone user to buy a commodity without cash and a card, and without entering a password. A personal authentication system includes a mobile phone, a reading adapter and an authentication server. The mobile phone can download a program for personal authentication from a web server. The mobile phone can, according to the downloaded program, output a train of serial optical pulses that represents personal information. The reading adapter can receive and read the output pulse train. The authentication server registers the personal information and performs personal authentication based on the read pulse train. In particular, Yamagishi describes a personal authentication system, in which a mobile phone is employed to download a personal authentication program and output a train of optical pulses according to the program to represent personal information.

In U.S. Patent Application No. 2003/0136837 to Amon et al (hereinafter merely Amon) describes a method and a system for the local or remote authentication of an item, in particular a security document, with the help of a authenticating device, comprised in, connected to, or linked to mobile communication equipment. Said item carries a marking exhibiting a characteristic physical behavior in response to interrogating energy, such as electromagnetic radiation and/or electric or magnetic fields. Said marking may comprise physical and logical security elements, e.g. a barcode, or a characteristic particle or flake pattern, exhibiting a characteristic physical response. In other words, a method is disclosed to use a mobile communication device for item authentication. The items, in particular security documents are authenticated through the methods of imaging, spectroscopy, barcode, radio-frequency resonance, etc. As can be seen, among various embodiments of the Amon patent application, only the imaging method utilizes a camera that integrated in the mobile phone. In other embodiments, the authentication devices are accessories that are linked to the mobile phone through wired or wireless connections.

In U.S. Patent Application No. 2005/0111723 to Hannigan et al, digital watermarking methods and systems are described. In one embodiment, a handheld device displays a digitally watermarked image at an event center. An optical scanner captures optical scan data representing the device display. A watermark decoder analyzes the captured optical scan data to obtain the watermark. The watermark is used to determine authorized entry. The handheld device may include a cell phone or other portable computing device. In other words, a handheld device, such as a cell phone, is used to display a digitally watermarked image for authorized entry.

In U.S. Patent Application No. 2006/0082760 to Lin describes an optical sensing module, an optical sensing and image capturing architecture, and a method for optically scanning fingerprints with a portable communications system associated with a mobile phone to capture a group of images of a fingerprint on a finger of the user of the mobile phone. The optical sensing module has a light permeable device, at least one light source, and a sensing device. The sensing device has a plurality of sensors that form a line array of sensors. The optical sensing and image capturing architecture has the above optical sensing module and an image output unit. The volume of the optical sensing module is reduced for facilitating installation in the portable communications system, for fragmentally capturing a group of images of the fingerprint, and for processing of identification of the fingerprint. In other words, an optical sensing and image capturing architecture is applied to a mobile phone to capture a group of images of a fingerprint for personal identification.

None of the above mentioned references disclosed a method of integrating an optical spectroscopic sensor with a mobile communication device and the numerous applications engendered thereof, which will be the main topic of the present invention.

SUMMARY OF THE INVENTION

A spectroscopic sensor that is integrated with a mobile communication device is provided.

A spectroscopic sensor that is integrated with a mobile communication device that is remotely communicable with a processor and/or database is provided.

A mobile communication device having a spectroscopic sensor integrated therewith is provided.

A mobile communication device having a spectroscopic sensor integrated therein is provided.

A mobile communication device, which is remotely communicable with a processor and/or database, having a spectroscopic sensor integrated therewith is provided.

A mobile communication device, which is remotely communicable with a processor and/or database, having a spectroscopic sensor integrated therein is provided.

A portable device having a mobile communication device associated with a mobile communication network, and a spectroscopic sensor integrated with the mobile communication device for measuring an optical spectrum of an object is provided, whereby the spectroscopic sensor utilizes the wireless communication network for sensed data processing or transmitting/receiving.

A method for integrating a spectroscopic sensor with a mobile communication device is provided. The method includes the steps of: providing a mobile communication device associated with a mobile communication network; and providing a spectroscopic sensor integrated with the mobile communication device for measuring an optical spectrum of an object, whereby the spectroscopic sensor utilizes the wireless communication network for sensed data processing or transmitting/receiving.

A portable device having a means for mobile communication associated with a mobile communication network, and a spectroscopic sensor means integrated with the means for mobile communication for measuring an optical spectrum of an object is provided, whereby the spectroscopic sensor means utilizes the wireless communication network for sensed data processing or transmitting/receiving.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to an optical spectroscopic sensor integrated with a mobile communication device thus forming a device having spectroscopic sensing and information transmitting/receiving capabilities. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Preferred embodiments of the present invention will now be set forth in detail with reference to the drawings.

Referring to FIGS. 1-9, a distributed spectroscopic sensor network 100 is illustrated which comprises a plurality of optical spectroscopic sensors 102 each integrated with a mobile communication device 104, such as a mobile phone. This integration enables the spectroscopic sensors 102 to transmit/receive data over the existing wireless communication network 106, which may further comprise relay towers 108 and central control offices 110. According to FIG. 1, wireless communication 114 is employed between mobile communication devices 104, mobile communication device 104 and relay tower 108, or between mobile communication device 104 and central control office 110. Wired communication 116 may be employed between central control offices 110. The spectroscopic sensor 102 collects optical spectral information from a physical object 112. The spectral information may be processed by a microprocessor (not shown) embedded in the mobile communication device 104 and/or exchanged among the spectroscopic sensors 102 or transmitted to the central control offices 110 for further analysis and decision making. The mobile communication device 104 may also be used to download data or programs from the central control office 110 for processing the spectral information obtained by the spectroscopic sensor 102. The structure of the spectroscopic sensor network 100 may take any topology that employed in a wireless communication network. For example, it can adopt a star configuration, which has a central office for data exchange and analysis. Or it can adopt a mesh configuration, which is de-centralized. In other cases, it can be a hybrid network combining wireless, wired and satellite communications.

Figure 1:
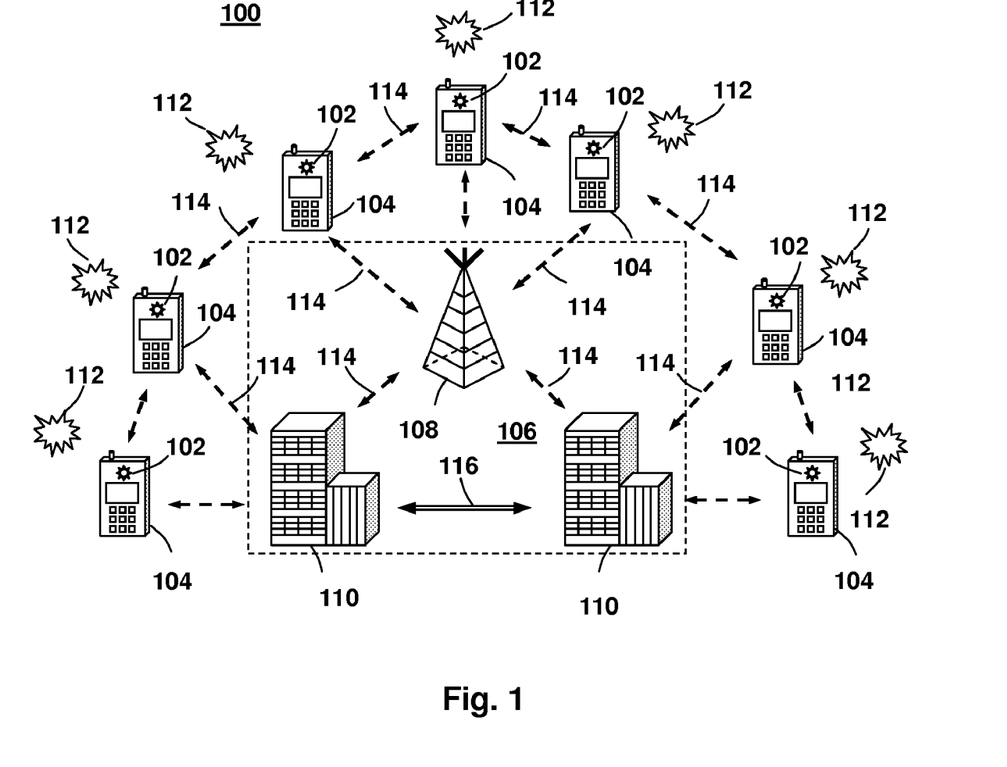
FIG. 1 illustrates an exemplified distributed sensor network utilizing mobile phone based spectroscopic sensors and an existing wireless communication infrastructure.

Due to its mobile nature, the sensor network 100 of the present invention is highly dynamic in size. The size of the sensor network may range from within a building, such as a local area network (LAN) to metropolitan or even global scale such as wide area network (WAN), metropolitan network (MAN). Positioning systems such as GPS (global positioning system) function that already exists in some mobile phones can be utilized to precisely locate and mark the position of each spectroscopic sensor so that an overview of the interested spectral information associated with precise coordination for an entire area is obtained.

Figure 2A:
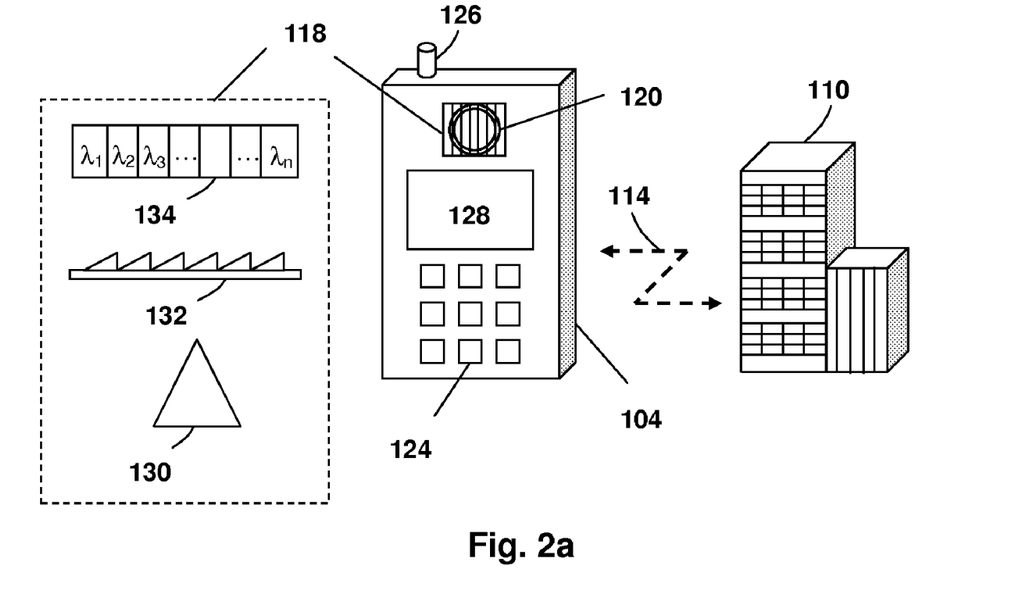
FIG. 2a illustrates the first embodiment of the present invention having a wavelength selective element being attached onto the lens of a camera mobile phone to form a spectroscopic sensor.

FIG. 2a illustrates the first preferred embodiment of the present invention, in which a spectroscopic sensor 102 of FIG. 1 is formed by attaching a wavelength selective element 118 in front of the lens 120 of a camera mobile phone 104. Camera mobile phone 104 comprises a built-in complementary metal oxide semiconductor (CMOS) or charge coupled device (CCD) image sensor 122, a dialing/input key pad 124, an antenna 126, and a LCD display 128. The wavelength selective element 118 can be a prism 130, a grating 132, or a linear variable filter 134. The wavelength selective element 118, in combination with the lens 120, and the CMOS/CCD image sensor 122, form a spectroscopic sensor 102 for analyzing the optical spectrum of a physical object 112. The spectroscopic sensor 102 shares the same LCD display 128 and key pad 124 with the mobile phone 104 for user interface, program control, and data input. The spectrum contemplated by the present invention comprises emission, reflection, diffusion or transmission spectrum. The obtained spectral information can be encoded by the mobile phone 104 and transmitted to other locations in the wireless communication network 106 via the antenna 126.

Figure 2B:
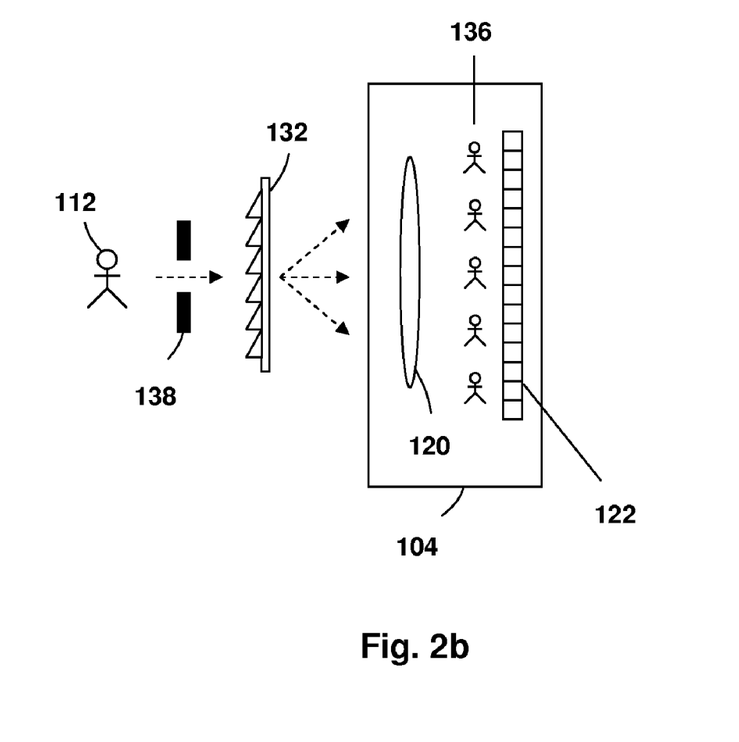
FIG. 2b illustrates the operation principle of the first embodiment, wherein a grating is used as the wavelength selective element.

A more detailed illustration of the spectroscopic sensor 102 is illustrated in FIG. 2b. In this example, a grating 132 is used as the wavelength selective element 118. The emission spectrum of the object 112 is first dispersed according to wavelength by the grating element 132. The dispersed light is then collected by the lens 120 and in turn forms multiple images 136 of the object 112 on different positions of the CMOS/CCD image sensor 122, wherein each image 136 corresponds to a particular wavelength component of the optical spectrum of the object 112. An entrance slit 138 may be inserted between the object 112 and the grating element 132 to achieve better spectral resolution. The obtained spectrum may be transmitted via wireless communication 114 to a central control office 110 with established database for a detailed analysis. The analysis results may be transmitted back to the holder of the spectroscopic sensor 102 for further actions. The grating 132 can be replaced by a prism 130, a linear variable filter 134 or any other suitable types of one-dimensional (1-D) or two-dimensional (2-D) optical filters.

Figure 3:
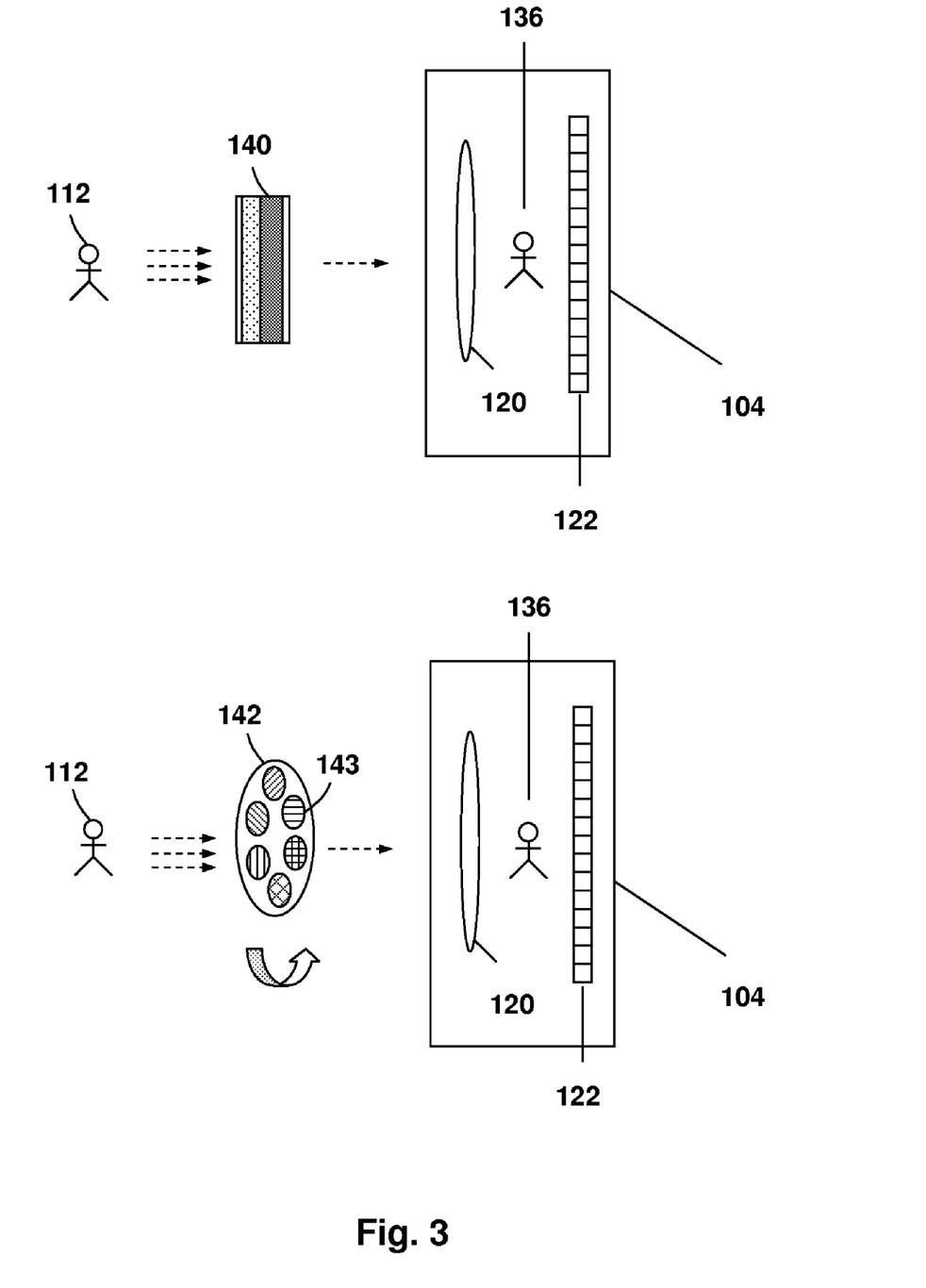
FIG. 3 illustrates another variation of the first embodiment, wherein a liquid crystal tunable filter or a rotating color wheel is used as a wavelength selective element to provide spectral imaging of the target.

Referring to FIG. 3, another variation of the first embodiment is illustrated, in which a tunable filter, such as a liquid crystal (LC) tunable filter 140, an acousto-optic tunable filter (AOTF) (not shown), or a rotating color wheel 142, is attached in front of the lens 120 of a camera mobile phone 104 for spectral imaging and analysis. Different wavelength components from the optical spectrum of a physical object 112 are first selected by the tunable filter and then projected onto the digital camera to form images 136 with different wavelengths or colors. Wavelength tuning or selection is achieved by varying the voltage applied on the liquid crystal for the LC filter 140 or by rotating the color wheel 142 which comprises a set of fixed filters 143 with different filtering wavelengths. A three-dimensional (3-D) (two spatial dimensions and one spectral dimension) spectral image of the object 112 may be formed by combining the images 136 corresponding to different wavelength components. The tunable filter used here is not limited to the above mentioned types. Any known tunable optical filter providing wavelength selectivity can be employed.

Figure 4:
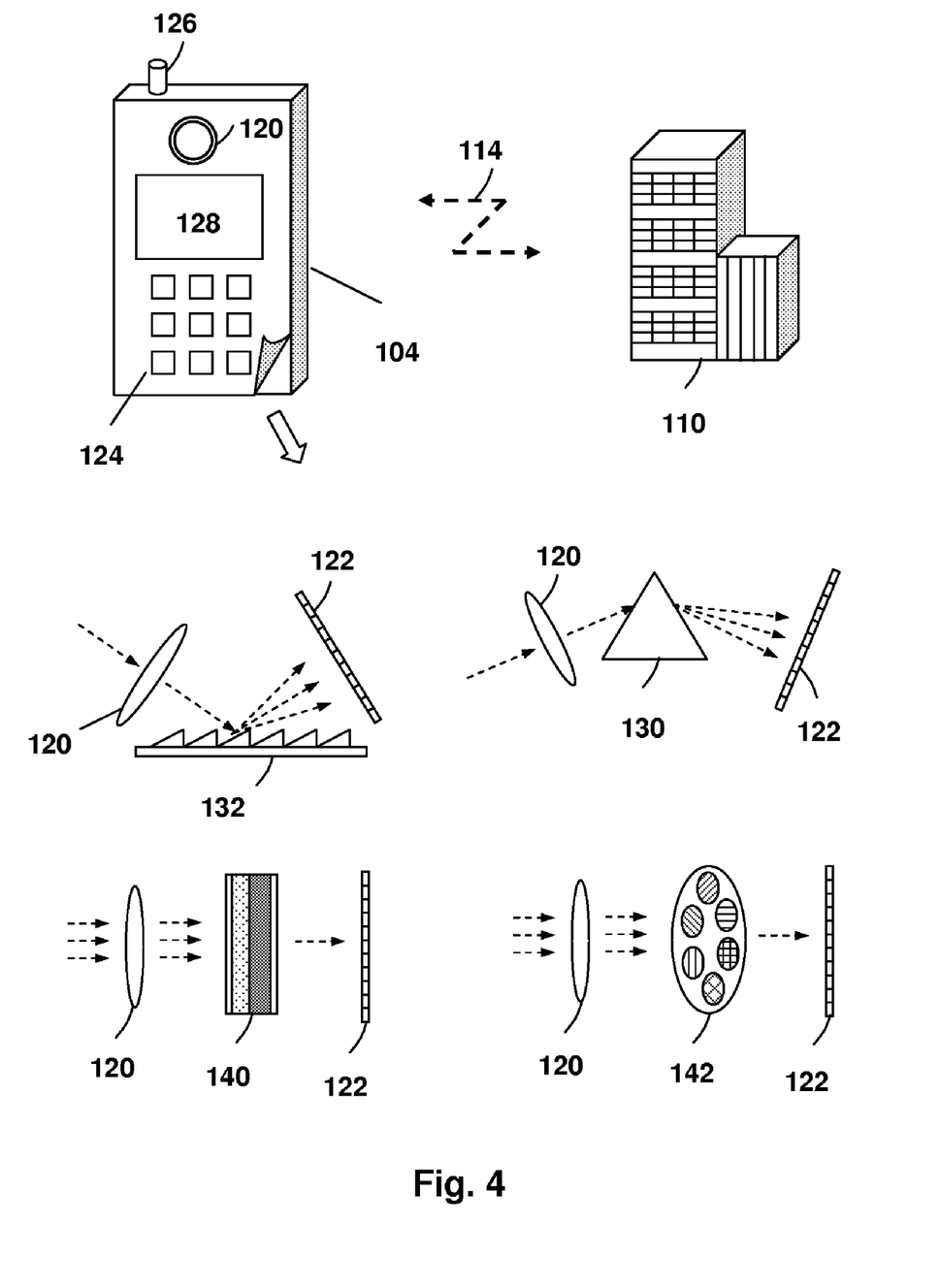
FIG. 4 illustrates the second embodiment of the present invention having a wavelength selective element being implemented inside a camera mobile phone to form a spectroscopic sensor.

In the second preferred embodiment of the present invention, a wavelength selective element is integrated within a camera mobile phone 104 in a position between the lens 120 and the CMOS/CCD image sensor 122. A schematic view of this embodiment is illustrated in FIG. 4. Here the wavelength selective element 118 can be a grating 132, a prism 130, an LC tunable filter 140, a color wheel 142 or any known wavelength selective elements described above. The function of this spectroscopic sensor 102 is similar to the one described in the first embodiment. By adopting suitable digital signal processing techniques to combine or process the spectral components of the image obtained on the CMOS/CCD sensor 122, the spectroscopic sensor can also be used as a normal or known digital camera.

Figure 5A:
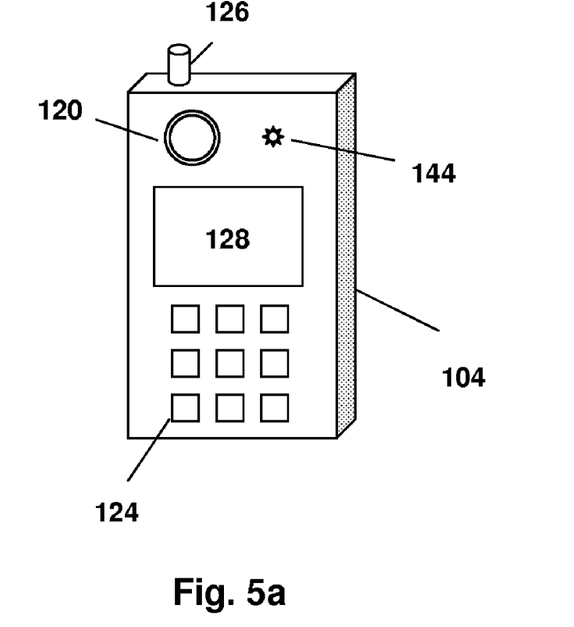
FIG. 5a illustrates the third embodiment of the present invention, wherein a LED light source is used to generate a reflection, scattering, or fluorescence emission spectrum from an object for spectral analysis.

Referring to FIG. 5a, in the third preferred embodiment of the present invention, the spectroscopic sensor 102 comprises a light emitting diode (LED) light source 144, a lens 120, a wavelength selective element (not shown), and a CMOS/CCD image sensor (also not shown), all integrated in a camera mobile phone. Here the LED light source 144 can be the flash lamp that already exists in a known camera mobile phone. The object 112 to be measured is first illuminated by the LED 144 to generate a reflection, scattering, or fluorescence emission optical signal. The optical signal is then collected by the lens 120 and dispersed or separated in wavelength domain by the wavelength selective element. The intensity of each wavelength component of the optical signal is finally measured by the CMOS/CCD image sensor. An optical filter can be further attached onto the LED 144 for excitation wavelength selection.

Figure 5B:
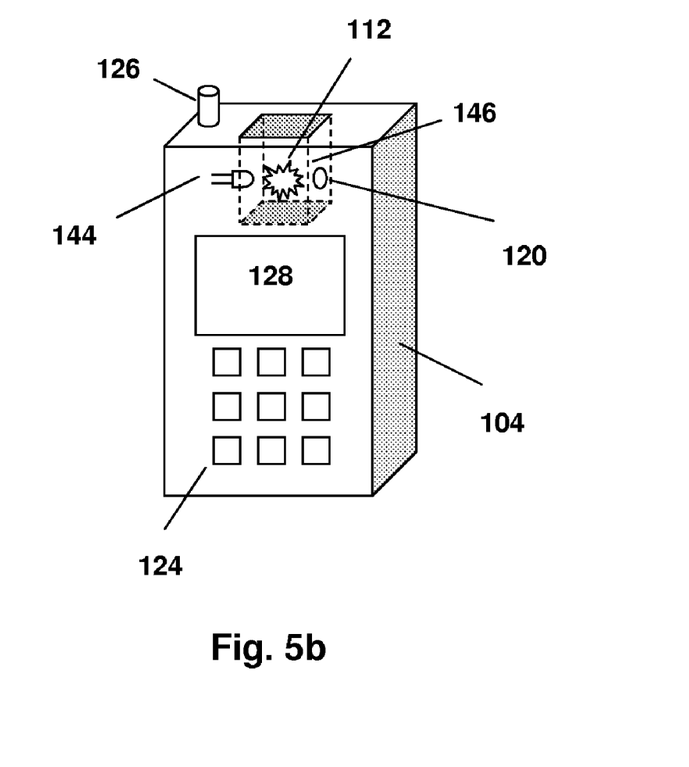
FIG. 5b illustrates another variation of the third embodiment, wherein the absorption or diffusion spectrum of an object is measured by the LED light source of FIG. 5a and the spectroscopic sensor.

In another variation the third embodiment as shown in FIG. 5b, the LED 144 and the lens 120 is positioned on opposite sides of an object 112 to measure its absorption spectrum. Here the object 112 may be placed in a transparent sample holder 146, such as a cuvette. In this configuration, the LED 144 is used as a broadband light source. When the light produced by the LED 144 transmits through the object 112, certain wavelength components of the LED light is absorbed, which produces an absorption spectrum. The transmitted light is then collected by the lens 120 and coupled into the spectroscopic sensor for spectrum analysis.

In the fourth preferred embodiment of the present invention, a laser or a spectrum-narrowed LED is utilized as the light source for the spectroscopic sensor 102. The laser can be a diode laser or a diode pumped solid state (DPSS) laser that is implemented in popularly known laser pointers. The laser can be integrated into a mobile phone based spectroscopic sensor in a way similar to that shown in FIG. 5a. The laser excites fluorescence emission, Raman scattering, and/or LIBS (Laser Induced Breakdown Spectroscopy) emission from the object 112 and the fluorescence/Raman/LIBS spectrum is measured by the spectroscopic sensor. The Raman signal is generally weaker than the fluorescence signal but sometimes it provides more structural information about the object. The Raman signal can be further enhanced through Resonant Raman Effect and/or Surface Enhanced Raman Effect.

Figure 6:
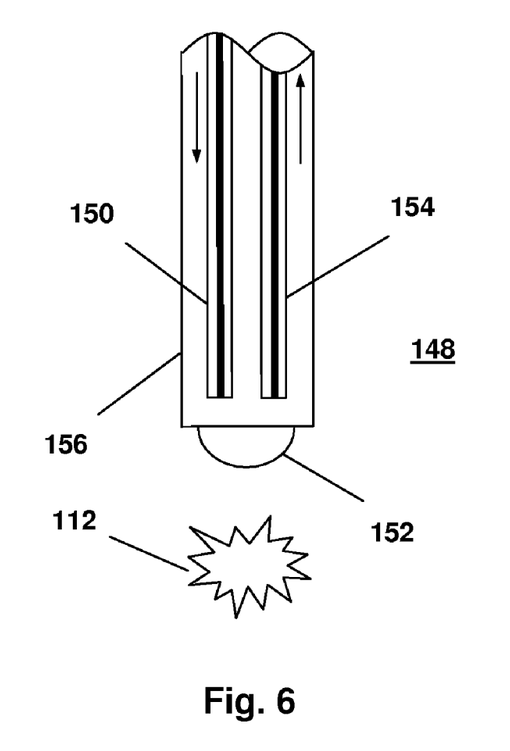
FIG. 6 shows a schematic view of a fiber optic probe as an accessory tool for the spectroscopic sensor.

In the fifth preferred embodiment of the present invention, a fiber optic probe 148 is used as an accessory tool of for the spectroscopic sensor 102 for use in remote spectrum analysis. An exemplary structure of the fiber optic probe 148 is illustrated in FIG. 6. The light from a laser, LED or other light sources is transmitted through an excitation optical fiber 150 to an object lens 152 positioned on the tip of the fiber optic probe 148. The light is focused on the object 112 by the objective lens 152 and is then reflected, scattered or absorbed by the object 112 produce a reflection, fluorescence, or Raman scattering light. The light from the object 112 is collected by the same object lens 152 and transmitted to the spectroscopic sensor 102 via a collection optical fiber 154 for spectrum analysis. The fibers 150 and 154 may be enclosed in a sheath 156 for protection purposes. Other components, such as filters, collimators, dichroic mirrors, etc., may be incorporated into the fiber optic probe for further improvement thereon.

In another variation, the excitation fiber 150 may be omitted and the fiber optic probe 148 is employed to collect the natural emission spectrum of the object 112. The fiber optic probe 148 is suitable for spectroscopy in adverse environments (such as operation under ultra high or low temperature, immersion into water or acid solutions, etc.). It is also useful for explosive or poisonous material detection where the operator needs to keep a safe distance away from the object 112.

According to one aspect of the present invention, an optical spectroscopic sensor is integrated with a mobile communication device, such as a mobile phone, for detection, identification, authentication, or monitoring of a physical object. The optical spectroscopic sensor comprises light sources, wavelength selective elements, and/or photo detectors or photo detector arrays. The spectroscopic sensor is capable of acquiring optical spectral information of the object. The spectral information comprises information obtained or acquired via emission, reflection, transmission, diffusion, fluorescence, and/or Raman spectra. Through the mobile phone, the obtained spectral information can, either be processed locally, or be transmitted, distributed, collected, and/or shared by utilizing all the functions of the known or future wireless communication networks. As an example, the spectral information can be sent to a remote office for storage, analysis, or decision making.

According to another aspect of the present invention, the optical spectroscopic sensor may utilize existing components on the mobile communication device as its building block. For example, the liquid-crystal display (LCD) of the mobile phone may be used as user interface. The key pad may be used for data input. The CMOS or CCD image sensor on a camera mobile phone may be used as the photo detector. The light emitting diode (LED) flash lamp on the camera mobile phone may be used as the light source. The lens of the camera mobile phone may be used for optical signal collection. The wavelength selective element of the spectroscopic sensor, which can be a dispersive grating, a prism, a set of fixed filters (such as a linear variable filter), or a tunable filter (such as a liquid crystal tunable filter), can either be integrated into the mobile phone in a position before the image sensor or be attached onto the lens of the camera mobile phone.

Applications of the disclosed spectroscopic sensor include real-time health status monitoring for human beings or other living creatures, environment monitoring, item authentication or identification, hazardous material detection/identification, forensic analysis, industrial process control, etc.

EXAMPLES OF PRACTICAL APPLICATIONS

Figure 7:
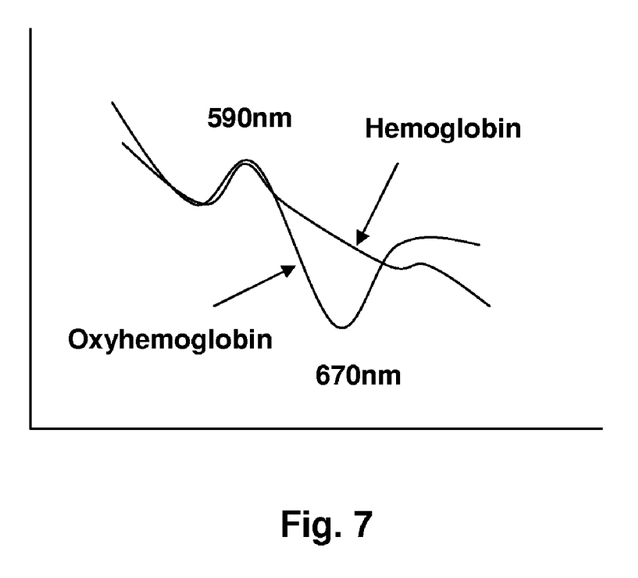
FIG. 7 illustrates the absorption spectra of hemoglobin and oxyhemoglobin.

One practical example of the disclosed spectroscopic sensor 102 is blood oxygen level measurement for real time human health status monitoring. In this application, the absorption spectrum of a living human tissue (such as a finger) is measured by the spectroscopic sensor 102 illustrated in FIG. 5b at visible and/or near infrared (NIR) wavelengths. To illustrate the method, FIG. 7 shows the typical absorption spectra for hemoglobin and oxyhemoglobin. The oxygen level of the blood, which is determined by the ratio of oxyhemoglobin content to hemoglobin content, can be inferred by comparing the absorption coefficients of the blood at two characteristic wavelengths. For example, one wavelength can be 590 nm where the absorption coefficients of hemoglobin and oxyhemoglobin are almost equal. The other wavelength can be 680 nm where the absorption coefficients of hemoglobin and oxyhemoglobin differ by an order of magnitude. With the integrated mobile phone, the measured blood oxygen level can be transmitted to a doctor or a hospital remotely located for real time patient health status monitoring. In case of emergency, the doctor or hospital can track the geographic location of the patient through the positioning capability of the mobile phone such as a global positioning system that already exists in some mobile phones or other known positioning schemes.

In another practical example, the spectroscopic sensor 102 is utilized to measure the level of protein, lipid, carotenoid or other chemical compounds of human skin. In this application, a diode laser is used as the light source to excite Raman scattering from the human skin. Using a spectroscopic sensor with a structure similar to that of FIG. 5a, the optical spectrum of the Raman scattering signal is measured. The obtained Raman spectrum, which is a complicated spectrum featuring multiple peaks that correspond to the vibrational and rotational modes of different chemical molecules and compounds, can be sent via the mobile phone 104 to a central office 110 for data analysis and comparing with an established database. Unlike conventional Raman spectrometers, this mobile phone based spectroscopic sensor 102 does not necessarily need a large memory to store the typical Raman spectra for different chemical compounds nor does it necessarily needs a full-functional central processing unit (CPU) to analyze or process the obtained Raman spectrum as functions and/or devices can be located or performed remotely to the sensor 102. This makes the spectroscopic sensor and the device that it integrates therein more compact in size and flexible in function, i.e. spectroscopic sensor 102 is not limited to measure only one particular chemical compound.

In yet another application of the present invention, the emission, transmission, diffusion, or reflectance spectrum of an object 112 is measured by the spectroscopic sensor 102 shown in FIGS. 2-5 for real time environment monitoring. For example, the variation of sun light spectrum after atmosphere transmission, which may be influenced by the absorption of water, ozone, $CO_2$ or other gases, can be used as an environment indicator. The existence of certain gas in the atmosphere can be identified from its characteristic absorption peak in the absorption spectrum. The integration of the spectroscopic sensor with the mobile phone makes it possible to build a nation wide ubiquitous environment monitoring system employing existing wireless communication infrastructures. The system can be easily deployed and/or reconfigured owing to the mobile nature of the spectroscopic sensor. Other spectral indicators, such as the absorption spectrum of water, can be used as well for the environment monitoring application.

In yet another application of the present invention, the spectroscopic sensor 102 is utilized for hazardous material detection and identification in airport, storehouse, and battlefield. The spectrum to be measured can be the fluorescence or Raman spectrum of the hazardous material that excited by a diode laser or LED. A fiber optic probe as shown in FIG. 6 may be used for remote spectrum collection. In case of battlefield, the variation of sun light spectrum can be utilized as an indicator for chemical and biological (CB) attack. The mobile spectroscopic sensors 102 provides a fast and convenient way for command center or headquarter to monitor the situation of a remote battlefield.

Figure 8:
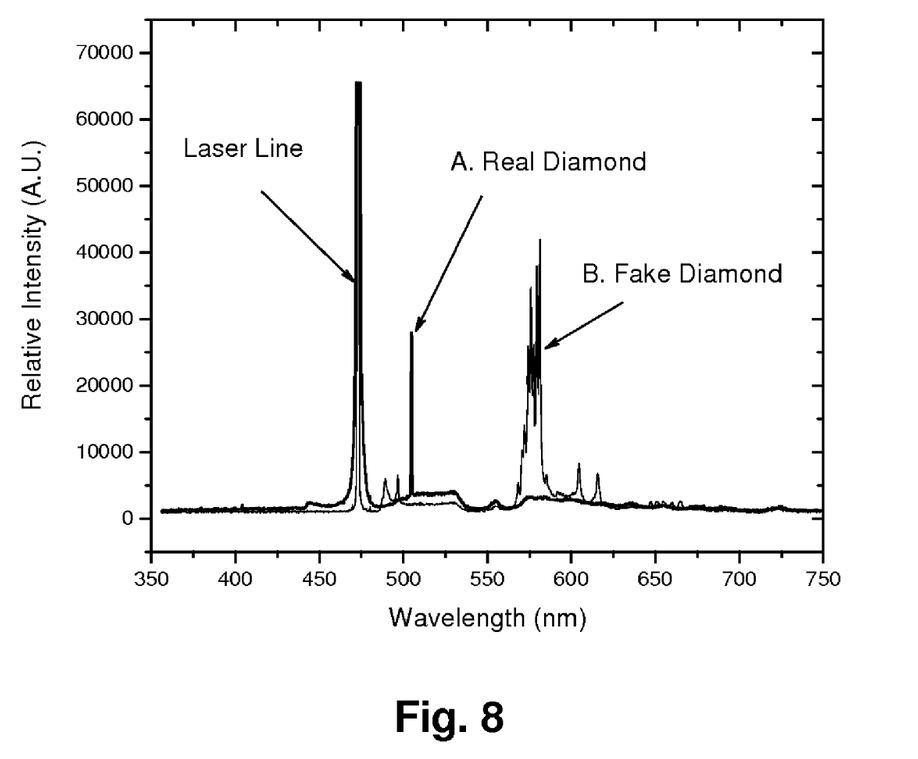
FIG. 8 shows the Raman spectra of a real and fake diamond sample.

In yet another application of the present invention, the spectroscopic sensor 102 is used for authenticating an object 112, such as currency, jewelry, or ID card. The object 112 can be authenticated by one of its constituents with special fluorescence spectrum, such as a special ink on the currency or ID, or it can be authenticated by its unique Raman scattering spectrum, such as for a diamond or other kinds of gem stones. As an example of this application, the Raman spectra of a real diamond and a fake diamond sample are shown in FIG. 8 curve A and B, respectively. The Raman spectra are excited by a DPSS laser at 473 nm. The real diamond can be easily identified by the unique diamond band at around 1332 cm$^{-1}$, which corresponds to 505 nm for the 473 nm laser excitation. In this application, a spectroscopic sensor with a structure shown in FIG. 5a can be employed. The wavelength selective element can be one described above or just a plurality of fixed filters for identifying a particular kind of object.

Figure 9:
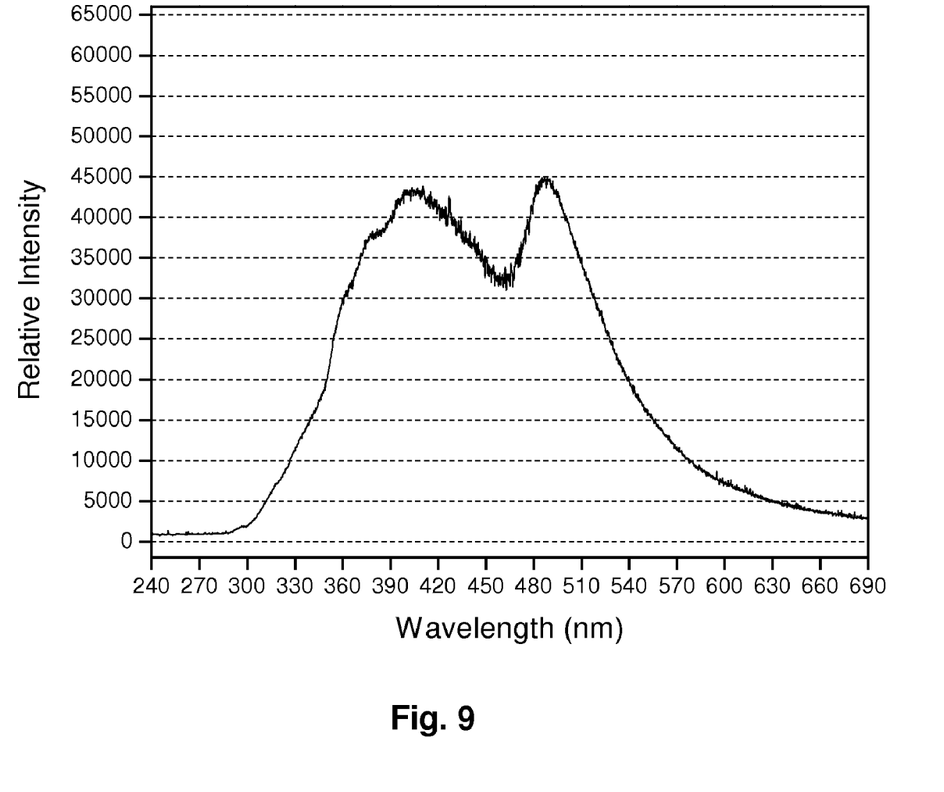
FIG. 9 shows the fluorescence emission spectrum of a crude oil sample.

In yet another application of the present invention, the spectroscopic sensor 102 is utilized as a tool to analyze the content of a target, such as food, mineral, crude oil, etc. As an example of this application, the fluorescence emission spectrum of a crude oil sample is shown in FIG. 9. The fluorescence spectrum is excited by an ultraviolet (UV) LED light source at 270 nm. The constitution and concentration of the crude oil can be extracted from the level and relative intensity of the fluorescence peaks.

In yet another application of the present invention, the spectroscopic sensor 102 provides a convenient means to determine the nutrition contents of fruits, vegetables, grains, etc. In this application, the fluorescence or Raman spectrum of the object 112 are measured by the spectroscopic sensor 102. The nutrition contents of the target are determined by the intensity of certain characteristic fluorescence or Raman scattering peaks in the fluorescence/Raman spectrum. The merits of this mobile spectroscopic sensor 102 include non-invasive detection, remote communication with established database, and ease of operation.

In yet another application of the present invention, the spectroscopic sensor 102 can be used for fast medical diagnosis and screening for on- or off-site point of care. For example, it can be used as a color sensor for precise determination and interpretation of the result of colored test strip of pregnancy testing. In other cases, the testing scheme can be developed with more color/gray scales since the spectroscopic sensor 102 can be more color sensitive in comparison to typical naked human eyes. Or in a more elaborated scheme, the optical spectrum change instead of color comparison is used in which a more precise measurement can be made.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A portable spectroscopic sensing device for measuring an optical spectrum of an optical signal, the device comprising:
   at least one wavelength selective element for separating the optical signal into a plurality of wavelength components; and
   a mobile communication device associated with a wireless communication network, said mobile communication device comprising a built-in digital camera for measuring the separated optical signal comprising the plurality of wavelength components and obtaining the optical spectrum of the optical signal;
   wherein the optical spectrum is transmitted through the wireless communication network;
   wherein said mobile communication device is a mobile phone.

2. The portable spectroscopic sensor of claim 1, wherein the wavelength selective element comprises a set of fixed filters.

3. The portable spectroscopic sensor of claim 1, wherein the wavelength selective element comprises at least one tunable filter.

4. The portable spectroscopic sensor of claim 1, wherein the wavelength selective element comprises at least one dispersive optical component.

5. The portable spectroscopic sensor of claim 1, further comprising a light source.

6. The portable spectroscopic sensor of claim 5, wherein the light source is a light emitting diode (LED).

7. The portable spectroscopic sensor of claim 5, wherein the light source is a laser.

8. The portable spectroscopic sensor of claim 1, further comprising a fiber optic probe for remote optical signal collection.

9. A method for measuring an optical spectrum of an optical signal, the method comprising the steps of:
   providing at least one wavelength selective element for separating the optical signal into a plurality of wavelength components; and
   providing a mobile communication device associated with a wireless communication network, said mobile communication device comprising a built-in digital camera for measuring the separated optical signal comprising the plurality of wavelength components and obtaining the optical spectrum of the optical signal;
   wherein the optical spectrum is transmitted through the wireless communication network;
   wherein the mobile communication device is a mobile phone.

10. The method of claim 9, wherein the wavelength selective element comprises a set of fixed filters.

11. The method of claim 9, wherein the wavelength selective element comprises at least one tunable filter.

12. The method of claim 9, wherein the wavelength selective element comprises at least one dispersive optical component.

13. The method of claim 9, further comprising providing a light source.

14. The method of claim 13, wherein the light source is a light emitting diode (LED).

15. The method of claim 13, wherein the light source is a laser.

16. The method of claim 9, further comprising providing a fiber optic probe for remote optical signal collection.

* * * * *